United States Patent [19]

Hayes

[11] 4,421,940
[45] Dec. 20, 1983

[54] PREPARATION OF NITROALKANES

[75] Inventor: William V. Hayes, Clute, Tex.

[73] Assignee: The Dow Chemical Company, Midland, Mich.

[21] Appl. No.: 352,506

[22] Filed: Feb. 25, 1982

[51] Int. Cl.³ .............................................. C07C 76/02
[52] U.S. Cl. ..................................... 568/948; 568/947
[58] Field of Search ................................ 568/947, 948

[56] References Cited

U.S. PATENT DOCUMENTS 3,115,527 12/1963 Drimus et al. ...................... 568/947

FOREIGN PATENT DOCUMENTS 578044 6/1946 United Kingdom ................ 568/947

OTHER PUBLICATIONS

Hass et al., J. Am. Chem. Soc., vol. 76, pp. 2692 to 2694 (1954).
Coldiron et al., Ind. Eng. Chem., vol. 50, pp. 991 to 992 (1958).

Primary Examiner—Leland A. Sebastian
Attorney, Agent, or Firm—A. C. Ancona

[57] ABSTRACT

An improved process for the vapor phase nitration of alkanes comprising feeding the alkane with an inert diluent gas and vaporizing the nitric acid on the surface of a catalyst bed which is the salt or oxide of a group II metal of the periodic chart.

10 Claims, No Drawings

PREPARATION OF NITROALKANES

BACKGROUND OF THE INVENTION

Nitroalkanes are an essential stabilizing ingredient employed in 1,1,1-trichloroethane when it is used in vapor degreasing and cold cleaning. All manufacturers throughout the world add nitromethane and/or nitroethane to their commercial 1,1,1-trichloroethane-based solvents. Normally nitro-paraffins are manufactured by a vapor phase nitration of the alkane with either nitric acid or $NO_2$. There is a mixture of products formed due to carbon-carbon scission. Thus, for example, when propane is nitrated, the products include 1-nitropropane, 2-nitropropane, nitroethane and nitromethane. Because of the oxidative conditions other oxygen containing compounds are also produced, e.g. aldehydes, acids and carbon oxides. Patents disclosing such a process are U.S. Pat. Nos. 2,844,634 and 2,905,724.

Improvements in these vapor phase nitrations are claimed by employing the nitric acid or nitrogen oxides together with oxygenated sulfur compounds, e.g. $SO_2$, $H_2SO_4$, (U.S. Pat. No. 3,272,874) and by conducting the nitration in the presence of ozone (U.S. Pat. No. 3,113,975).

Other processes involve nitration of paraffins by nitrogen peroxide $(NO_2)_2$ in the presence of oxygen (air) under pressure at 150°-330° C. (U.S. Pat. No. 3,780,115); reacting an olefin with nitric acid in the presence of a lower aliphatic monocarboxylic acid anhydride to produce a nitroester, subsequently reducing it with an alkali borohydride to form the nitroalkane (U.S. Pat. No. 3,706,808) and reacting organic amines with ozone (U.S. Pat. No. 3,377,387).

Another process, the subject of my copending application (with another) Ser. No. 211,017, filed Nov. 28, 1980, now abandoned, is an improvement which reduces the amount of by-products and obtains improved yields of the desired products by the nitrating of paraffins with nitric acid at lower temperatures and pressures in the presence of high intensity light.

It has now been discovered that methane or ethane can be reacted with nitric acid in the vapor phase with an inert diluent gas at high temperatures, >300° C., over a catalyst, e.g. $SrCl_2$ on a low surface area alumina.

SUMMARY OF THE INVENTION

An improved process for the nitration of paraffins especially methane and ethane in the vapor phase involves the use of an inert diluent gas, e.g. nitrogen, and a catalyst which is a salt or an oxide of a metal from Group II of the periodic table, e.g. $CaCl_2$ or $Sr(NO_3)_2$. The catalyst may be supported on an inert support, e.g. alumina of low surface area. The nitric acid is fed as a liquid and vaporized on the catalyst.

DETAILED DESCRIPTION OF THE INVENTION

The process is preferably conducted using the lower alkanes, particularly methane and ethane. These gases are mixed with an inert diluent which may be nitrogen, argon, carbon monoxide or carbon dioxide and passed over the catalyst together with liquid nitric acid which is thereby vaporized.

The gases but not the nitric acid are preferably preheated to a temperature of from about 200° to about 400° C. depending upon the alkane used. The bed of catalyst is maintained at a temperature of from about 325° to about 390° C. for ethane, 380° to about 425° C. for methane. The molar ratio of alkane employed is from about 0.5 to about 2 moles per mol of nitric acid. The preferred ratio is about one to one.

The catalyst may be particulate, e.g. pelleted, salts of metals of Group II of the periodic table, namely magnesium, calcium, strontium and barium. Salts of these metals, including the chlorides, sulfates, and nitrates may be employed. The oxides of the same metals are also useful.

Either the oxides or salts may also be burdened on an inert support and used in this manner. Methods of making supported catalysts are well known to the art. For example the support may be impregnated by immersing it in a salt solution or by spraying the solution, or slurry in the case of oxides or insoluble salts, onto the support.

Pressures employed in the process may be from about 1 to about 30 psig and preferably form about 6 to about 10 psig.

Because of the exothermic nature and flammable hazard involved in this reaction it is necessary to use a diluent. The diluent is normally employed in an amount of about 50 –60% of the total volume of gas fed, i.e. the alkane and nitric acid (as vapor) plus diluent. It is preferred to use at least about 54% diluent so as to be outside the flammability range.

The use of a catalyst makes it possible to conduct this known nitration reaction at lower temperatures and with better conversions and yields than are known to the art.

An example of one method of preparing the catalyst is as follows:

PREPARATION

A quantity of 300 g of a commerical grade of alumina (3/16" spheres, having a surface area of 0.02-0.2 m²/g) were immersed in a solution of 100 g $Sr(NO_3)_2$ in 250 ml of water. Excess solvent was evaporated off and the wet support heated with stirring in a pan at about 100° C. for one hr. and thereafter heated in an oven at 150° C. for two hours to dry the catalyst. The finished catalyst contained 22.2% $Sr(NO_3)_2$ by weight.

USE OF THE CATALYST

Examples 1-4

A quantity of 150 cc of the above prepared catalyst was placed in a 18"×1" pipe (316 stainless steel) reactor. The pipe was heated in a fluidized sand bed to a temperature of 425° C. and a mixture of methane and nitrogen in a ratio of ½ was preheated to about 250° C. and passed through the tube at a pressure of 7 psig. Liquid nitric acid (conc.) without any preheating was fed into the gas stream just above the catalyst bed. Flowrates were 3200 ml/min. nitrogen, 0.0625 gmol/min. methane and 0.0600 gmol/min. $HNO_3$, and contact time (C.T.) was 0.7 sec. The effluent gases were fed to a chilled water scrubber (10° C.). Methane conversion (conv.) was 8.2% and selectivity (sel.) to nitromethane (NM) 41.1%. Productivity (prod.) was calculated to be 80 pounds/day/ft³ of catalyst.

Using the same catalyst and reactor, with the same reactor and preheat temperatures, different feed rates and contact times were employed. These results are shown in Table I.

TABLE I

| Ex. # | CH$_4$ (gmol/ min) | HNO$_3$ (gmol/ min) | CH$_4$/ HNO$_3$ Ratio | C.T. (Sec) | CH$_4$ Conv. (%) | NM Sel. (%) | #/day/ ft$^3$ NM Prod. |
| --- | --- | --- | --- | --- | --- | --- | --- |
| 2 | .0446 | .0630 | 0.71 | 0.8 | 9.1 | 37.2 | 55 |
| 3 | .0446 | .0425 | 1.05 | 1.0 | 8.4 | 35.4 | 50 |
| 4 | .0580 | .0560 | 1.04 | 0.8 | 8.9 | 38.1 | 73 |

Examples 5–8

A catalyst support of the same alumina used in the previous examples was burdened with 25.8% SrCl$_2$ in the same manner as above. Ethane was used in the feed in place of methane and the feed was preheated to 195° C. and reacted at 335° C. Both nitromethane (NM) and nitroethane (NE) were obtained as products. Flowrates, contact time (C.T.) and results are shown in Table II.

TABLE II

| Ex. # | C$_2$H$_6$ (gmol/ min) | HNO$_3$ (gmol/ min) | C$_2$H$_6$/HNO$_3$ Ratio | C.T. (Sec) | C$_2$H$_6$ Conv. (%) | Sel. (%) |
| --- | --- | --- | --- | --- | --- | --- |
| 5 | .0178 | .0123 | 1.45/1 | 1.93 | 7.9 | 23.1 (NM) 63.5 (NE) |
| 6 | .0178 | .0178 | 1/1 | 2.06 | 8.1 | 22.8 (NM) 63.9 (NE) |
| 7 | .0178 | .0178 | 1/1 | 2.41 | 13.5 | 18.7 (NM) 51.4 (NE) |
| 8 | .0245 | .0167 | 1.47/1 | 1.89 | 9.9 | 16.9 (NM) 56.9 (NE) |

Examples 9–11

In the same manner as above a catalyst of CaCl$_2$ on a spherical alumina support ($\frac{1}{4}''$ diameter and a surface area of 0.03 m$^2$/g) was loaded into a tubular stainless steel reactor ($4' \times \frac{3}{4}''$). Preheat temperature in Examples 9 and 10 was 200° C. and reactor temperatures were 355° C. and 348° C., respectively. Example 11 was preheated to 230° C. and reacted at 360° C. Ethane was fed in Examples 9 and 10, while methane was fed in Example 11. Feed rates, contact times and results obtained are given in Table III.

TABLE III

| Ex. # | C$_2$H$_6$ (gmol/ min) | HNO$_3$ (gmol/ min) | C$_2$H$_6$/HNO$_3$ Ratio | C.T. (Sec) | C$_2$H$_6$ Conv. (%) | Sel. (%) |
| --- | --- | --- | --- | --- | --- | --- |
| 9 | .0178 | .0117 | 1.5/1 | 1.9 | 14.7 | 13.7 (NM) 43.6 (NE) |
| 10 | .0178 | .0117 | 1.5/1 | 1.9 | 9.9 | 14.7 (NM) 48.9 (NE) |
| 11 | .0134 | .0117 | 1.14/1 | 2.28 | 10.9 | 17.2 (NM) |

Examples 12–14

In these examples (using the same reactor as in Examples 9–11, above) different ratios of ethane/nitric acid were employed. A preheat temperature of 280° C. was used in each example and reactor temperatures were 385°, 390° and 393° C., respectively, for Examples 12, 13 and 14. The catalyst employed was 150 ml of #5 mesh anhydrous CaCl$_2$. Parameters and results are shown in Table IV.

TABLE IV

| Ex. # | C$_2$H$_6$ (gmol/ min) | HNO$_3$ (gmol/ min) | C$_2$H$_6$/HNO$_3$ Ratio | C.T. (Sec) | C$_2$H$_6$ Conv. (%) | Sel. (%) |
| --- | --- | --- | --- | --- | --- | --- |
| 12 | .0178 | .013 | 1.37/1 | 1.2 | 11.9 | 8.2 (NM) 19.5 (NE) |
| 13 | .0178 | .019 | 0.94/1 | 1.14 | 14.8 | 9.6 (NM) 21.8 (NE) |
| 14 | .013 | .0228 | 0.59/1 | 1.11 | 18.9 | 11.0 (NM) 24.2 (NE) |

I claim:

1. In a process for making nitroalkanes by reacting an alkane with nitric acid in the vapor phase in the presence of an inert diluent gas, the improvement which comprises employing a catalyst of a salt or oxide of a metal of Group II in the periodic chart of the elements.

2. The process of claim 1 wherein the metal is calcium or strontium.

3. The process of claim 1 or 2 wherein the catalyst is burdened on an inert low surface area support.

4. The process of claims 1 or 2 wherein the reaction is conducted at a temperature of from about 300° C. to about 430° C.

5. The process of claim 4 wherein the temperature is from about 325° to about 425° C.

6. The process of claim 4 wherein the molar ratio of alkane to nitric acid is from about 0.5 to about 2 to 1.

7. The process of claim 6 wherein the diluent gas makes up about 50 to 60% of the total volume of gas fed to the reactor.

8. The process of claim 7 wherein the volume of diluent gas is at least 54% of the total volume.

9. The process of claim 7 wherein the alkane is methane or ethane.

10. The process of claim 8 wherein the flowrate of the methane or ethane is such as to provide a contact time of from about 0.5 to about 3 seconds.

* * * * *